United States Patent [19]

Poirier et al.

[11] 4,363,328

[45] Dec. 14, 1982

[54] INHALATION EXERCISER

[75] Inventors: Victor L. Poirier, Chelmsford; Stanley D. Buczak, Billerica; Robert F. Lynch, Newburyport; Thomas R. Salvo, Brookline, all of Mass.

[73] Assignee: Thermo Electron Corp., Waltham, Mass.

[21] Appl. No.: 204,102

[22] Filed: Nov. 5, 1980

[51] Int. Cl.³ ............................................. A61B 5/08
[52] U.S. Cl. ..................................... 128/728; 272/99
[58] Field of Search ........... 128/728, 727, 725, 205.16; 272/99

[56] References Cited

U.S. PATENT DOCUMENTS

| | | | |
|---|---|---|---|
| 2,569,849 | 10/1951 | Emerson | 128/2.08 |
| 3,621,842 | 11/1971 | Manley | 128/205.16 |
| 3,722,506 | 3/1973 | McMillan, Jr. | 128/2.08 |
| 3,769,967 | 11/1973 | Jones et al. | 128/2.08 |
| 3,826,247 | 7/1974 | Ruskin et al. | 128/2.08 |
| 3,848,583 | 11/1974 | Parr | 128/2.08 |
| 4,025,070 | 5/1977 | McGill et al. | 272/99 |
| 4,060,074 | 11/1977 | Russo | 128/2.08 |
| 4,096,855 | 6/1978 | Fluery, Jr. | 128/2.08 |
| 4,114,608 | 9/1978 | Russo | 128/2.08 |
| 4,241,740 | 12/1980 | Brown | 128/728 |
| 4,299,236 | 11/1981 | Poirier | 128/728 |
| 4,323,078 | 4/1982 | Heimlich | 128/728 |
| 4,324,260 | 4/1982 | Puderbaugh | 128/728 |

OTHER PUBLICATIONS

G. D. Gale et al., "The Bartlett-Edwards Incentive Spirometer: A Preliminary Assessment of its Use in the Prevention of Atelectasis After Cardio-Pulmonary Bypass", *Canad. Anaesth. Soc. I*, vol. 24, No. 3, May 1977, pp. 408-416.

"The Challenger Incentive Spirometer Measures Volume, Not Flow", Advertisement in *American Hospital Supply*, May/Jun. 1980, p. 4.

"VOLUREX Opens a New Era in Volume Measured Respiratory Exercise", one page magazine advertisement, date uncertain but thought to be Jan./Feb. 1980.

"U-MID/VOLUME PLUS Respiratory Exerciser", two page magazine advertisement, date uncertain but thought to be Jan./Feb. 1979.

U.S. patent application Ser. No. 87,288, "Incentive Breathing Exerciser", Victor L. Poirier, filed Oct. 22, 1979.

*Primary Examiner*—Lee S. Cohen
*Attorney, Agent, or Firm*—Herbert E. Messenger; James L. Neal

[57] ABSTRACT

An inhalation device for use in breathing exercises is described. The exerciser includes a thin-walled bellows whose upper end is attached to a top housing member and whose lower end deflects upward upon withdrawal of air from an opening in the upper end of the bellows. Deflection of the bellows allows accurate measurement of the volume of air inhaled by a patient and a true indication whether an inhaled breath is being held. Slotted support arms connecting the top housing member and a bottom housing member permit collapse of the device for storage and shipment of the exerciser as a compact unit. A weight attached to the lower end of the bellows provides a biasing force to assure return of the bellows to a fully extended position even after long-term storage of the device in collapsed form.

8 Claims, 6 Drawing Figures

INHALATION EXERCISER

CROSS REFERENCE TO RELATED APPLICATION

Some of the subject matter of the present invention is related to that disclosed in U.S. application Ser. No. 87,288, Incentive Breathing Exerciser, filed Oct. 22, 1979, from which U.S. Pat. No. 4,299,236 issued on Nov. 10, 1981 and assigned to the assignee of the present invention.

BACKGROUND OF THE INVENTION

This invention relates to an inhalation device or incentive breathing exerciser for use in respiratory therapy.

A recognized technique for treating patients with respiratory deficiencies or patients recovering from thoracic or abdominal surgery is the use of breathing exercisers. Such devices enable patients to strengthen and more fully utilize their respiratory systems, thus hastening recovery and avoiding complications such as pneumonia and lung collapse.

Among the inhalation devices presently known is that disclosed in U.S. Pat. No. 4,114,608. In using this device, a patient inhales through a tube connected near the bottom end of a container with a cylindrical wall and dome-shaped ends. Inhalation causes air to be drawn into the top end of the container through a port, then across the top end and into a larger port of a passageway leading down the wall to the breathing tube. The venturi effect associated with airflow between the ports causes a lightweight ball to rise from the bottom of the container, and continued inhalation keeps the ball suspended.

While the above-mentioned patent and references cited therein disclose a number of improvements in breathing exercisers such as reduced cost and complexity, the devices described cannot readily be used in certain types of respiratory therapy. For example, since many prior art devices respond to inhalation rate, they are ill-suited for measuring the actual volume of air inhaled by a patient or for use in exercises wherein a patient takes a breath and holds the breath for a prescribed time interval. The holding of a deep breath for a measured time such as 2-4 seconds has been recognized as a valuable aspect of respiratory therapy.

Inhalation devices which measure the actual volume of air inhaled by a patient, although desirable, present certain difficulties because of the many criteria they must satisfy. Such devices must have sufficient size to accommodate the volume of air inhaled by a patient. On the other hand, since most inhalation exercisers are intended for use by a single patient and thus are manufactured and purchased in large numbers, it is important that the exercisers be convertible to a compact form to minimize shipping and storage requirements. If inhalation exerciser units are collapsible or capable of disassembly for compact storage, re-assembly of the units for use should be simple. Also, storage of the units for reasonable time periods must not impair their proper operation.

Accordingly, it is an object of the invention to provide an inhalation device for accurately measuring the volume of air by a patient.

It is an object of the invention to provide an inhalation exerciser for accurately measuring the volume of air inspired by a patient and for verifying that an inhaled breath is being held by the patient.

It is an object of the invention to provide an inhalation device which, in addition to the foregoing, is inexpensive, storable in compact form, and easy to assemble.

It is an object of the invention to provide an inhalation device for accurately measuring the volume of air inspired by a patient, and which is collapsible without removal of major components and which is storable in collapsed form for appreciable time periods without impairment of operation.

SUMMARY OF THE INVENTION

The invention concerns a breathing exerciser having a lightweight bellows whose deflection allows measurement of the air inhaled by a patient during respiratory therapy. The upper end of the bellows is attached to a top housing member and has a port through which air may be drawn, preferably by means of an inhalation tube attachable to the top housing member. During inhalation, upward deflection of the movable lower end of the bellows along a scale towards the top housing member permits accurate measurement of the true volume of air inhaled by a patient.

A preferred inhalation device according to the invention includes a thin-walled bellows of square cross-section positioned between a top housing member and a bottom housing member, and a pair of side support arms on opposed sides of the bellows for supportably connecting the housing members. At least one of the support arms has a scale which may be aligned with the movable lower end of the bellows to indicate the true volume of air inspired by the patient. Each support arm also includes an elongated slot shaped to receive and hold ear-like tabs projecting from opposed sides of the top and bottom housing members. The tabs and slots permit rotational and sliding movement of the housing members relative to the side arms to permit conversion of the device from a deployed form suitable for breathing exercises to a collapsed, compact form suitable for storage.

The deployed exerciser has its side arms oriented parallel to the direction of movement of the bellows during inhalation, and its top and bottom housing members are locked at opposite ends of the elongated slots of the side arms. By contrast, the exerciser in collapsed form has its side arms normal to the direction of movement of the bellows during inhalation, and its housing members are adjacent each other. Conversion from one form to another is simple and is accomplished without disconnecting the side arms from the housing members.

Retention of the thin-walled bellows in collapsed form for a period of time such as during shipment or storage may result in the bellows acquiring a cold set, particularly if the bellows are formed of a plastic material such as polyethylene. Accordingly, the exerciser preferably includes biasing means such as a weight attached to the lower end of the bellows to assure return of the movable lower end of the bellows to its fully extended position during use of the device after its storage in collapsed form.

The inhalation device of the invention is particularly suited for exercises wherein a patient takes a breath of a prescribed volume and holds the breath for an interval of time. Since the bellows is airtight except for the inhalation port in its upper end, the volume indicated by deflection of the lower end of the bellows is the true volume inhaled. Also, the bellows remains in its deflected position for as long as the breath is held.

DETAILED DESCRIPTION OF A PREFERRED EMBODIMENT

Figure 1:
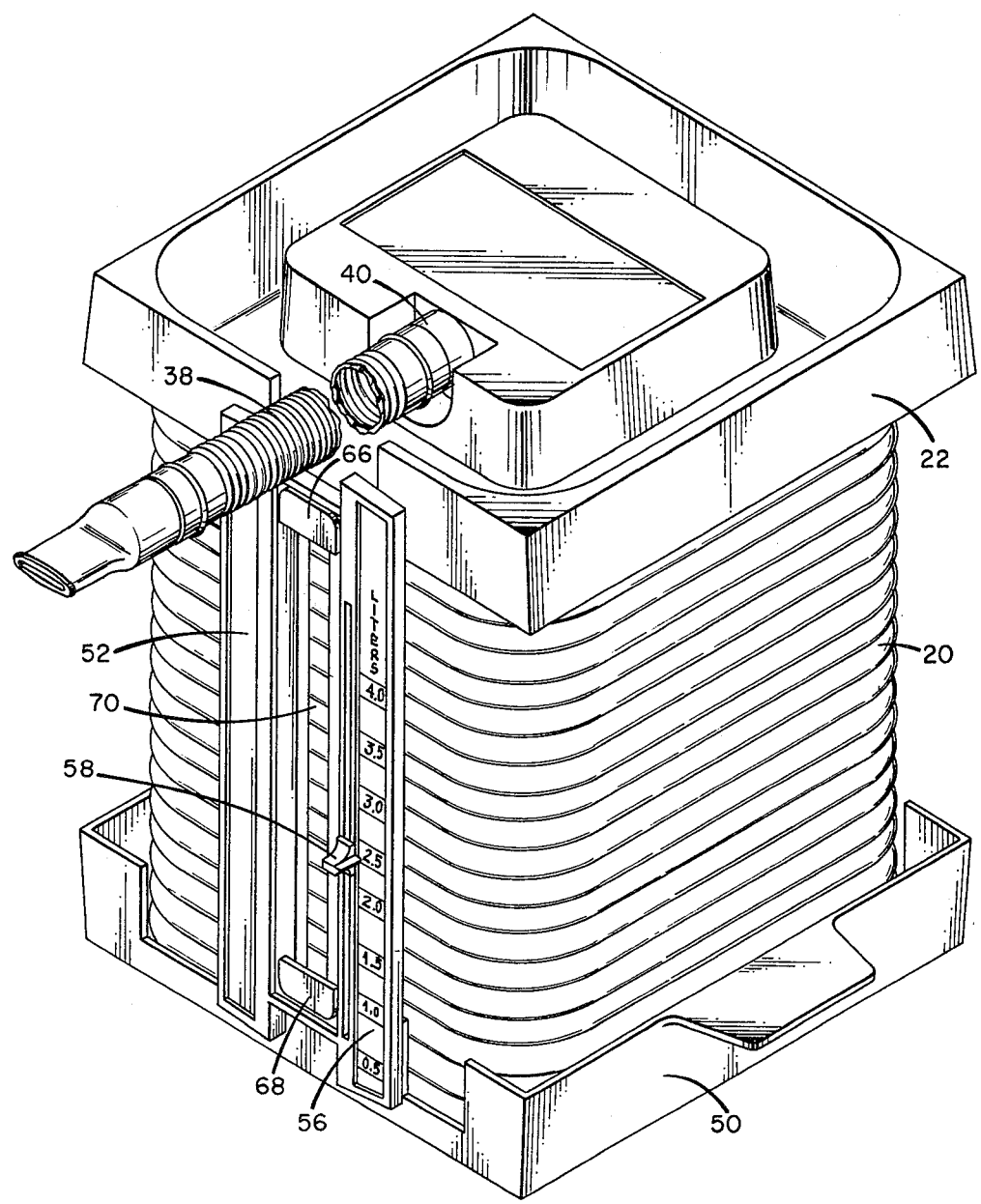
FIG. 1 is a perspective view of a preferred embodiment of the invention illustrating an inhalation device deployed for use.
Figure 2:
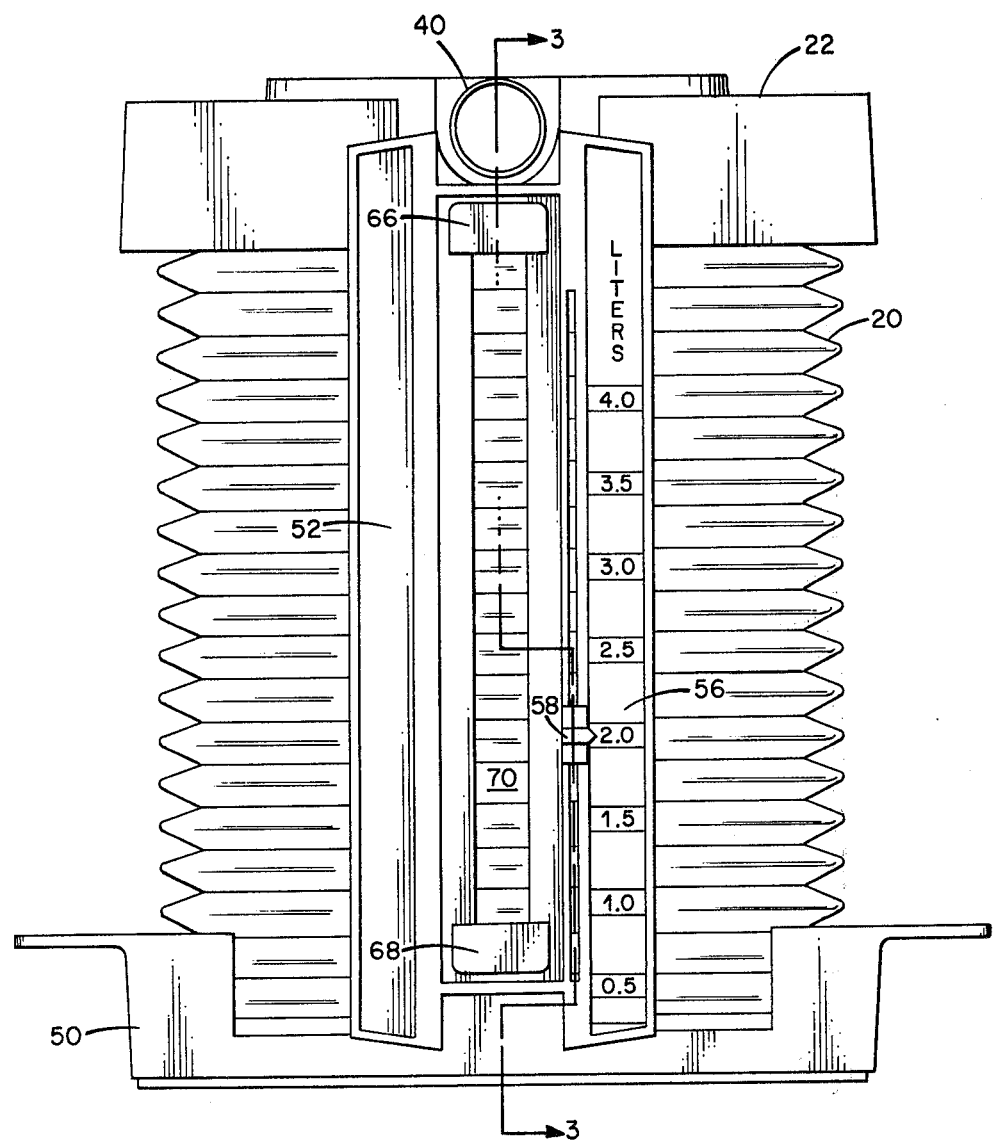
FIG. 2 is a side view of the inhalation device deployed for use and with the bellows fully extended.
Figure 3:
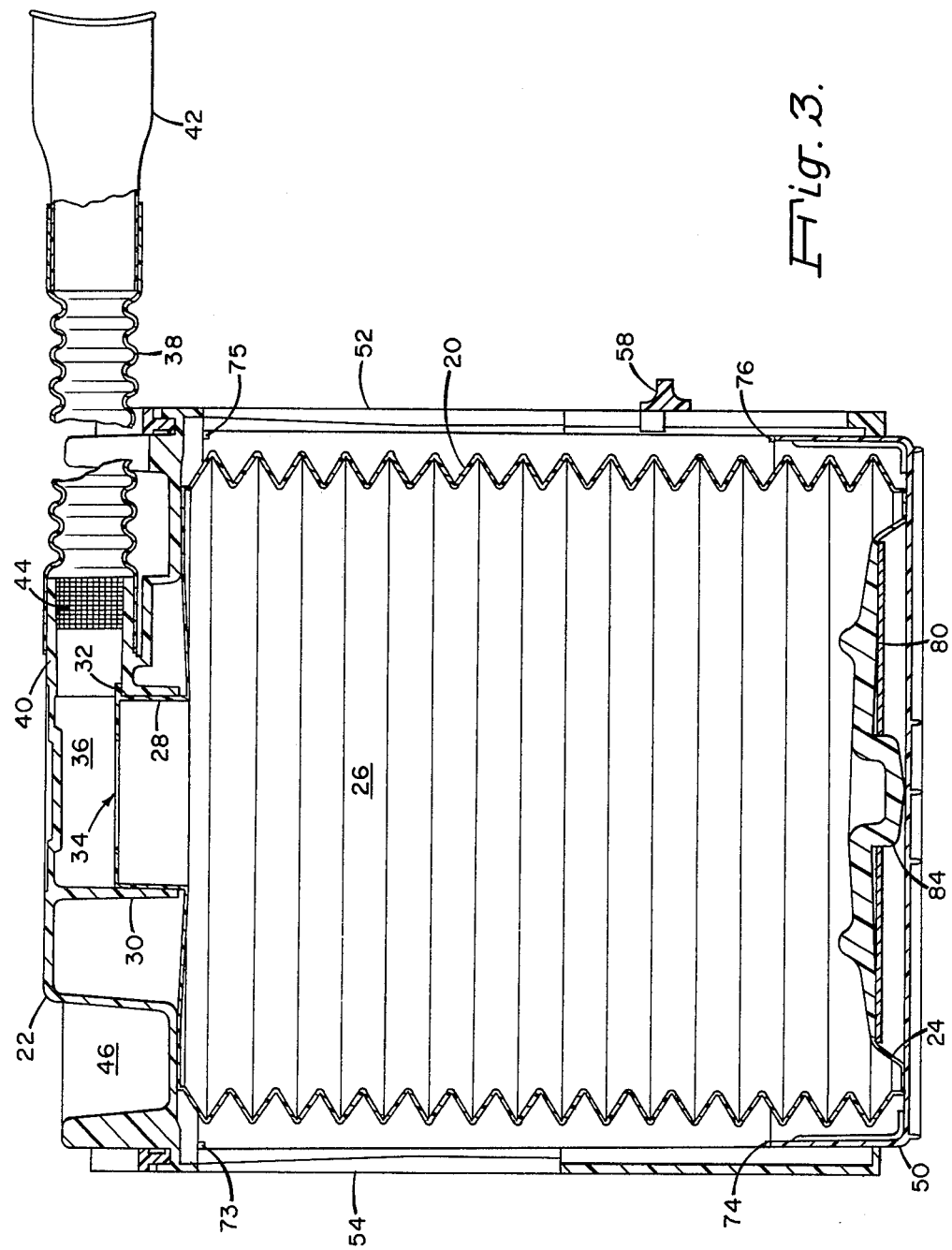
FIG. 3 is a cross-sectional view of the inhalation device taken along the lines 3—3 of FIG. 2.
Figure 4:
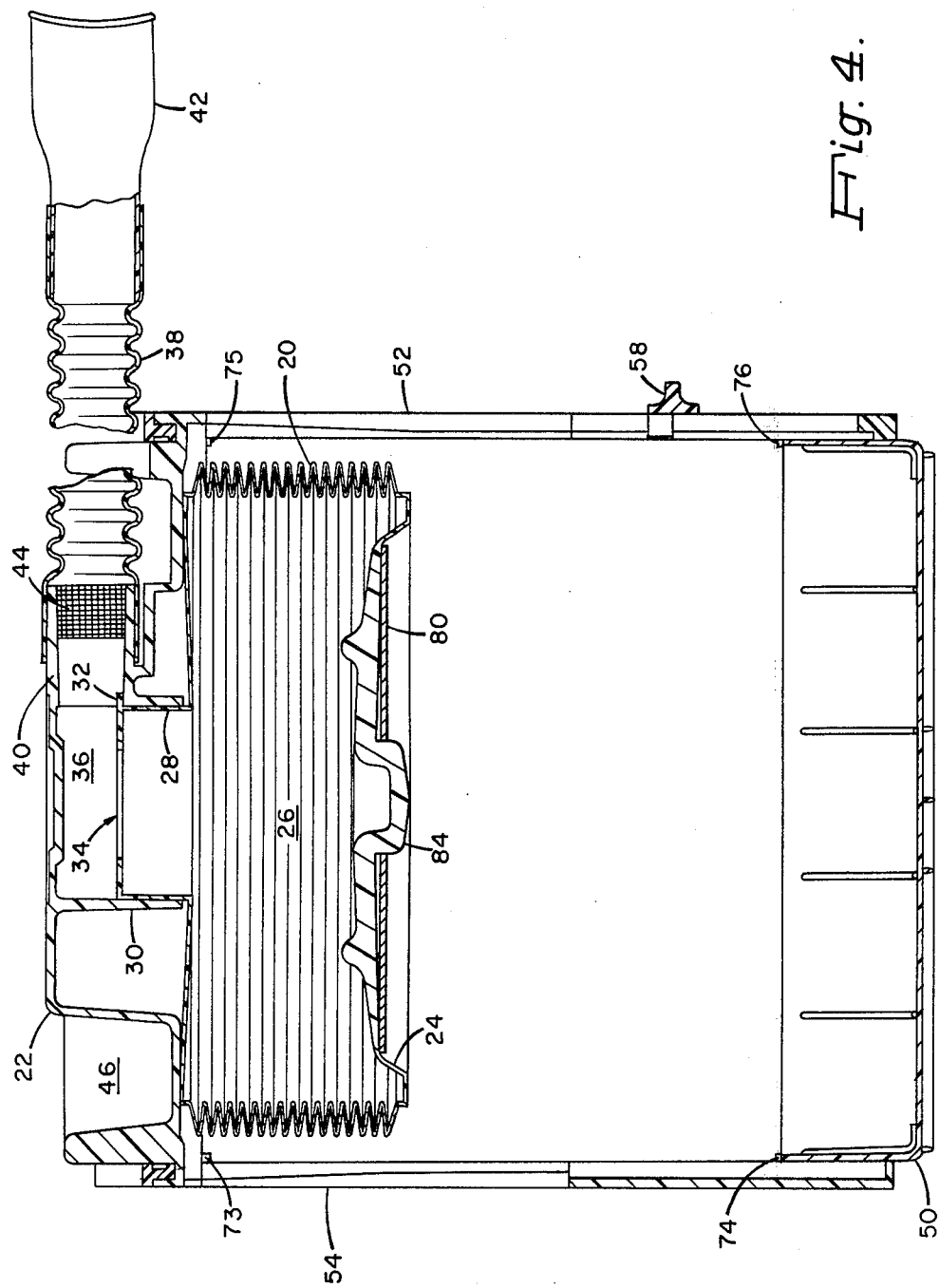
FIG. 4 is a cross-sectional view of the inhalation device during use showing the bellows in a partially retracted position.

A preferred inhalation device according to the invention is shown in FIGS. 1-3, which illustrate the device deployed for use in breathing exercises. The inhalation exerciser comprises a thin-walled bellows 20 whose upper end is attached to a top housing member 22 and whose lower end 24 is movable in response to inhalation from an extended position as shown in FIGS. 1-3 to a retracted position wherein the lower end 24 is adjacent to the top housing member 22 (FIG. 4).

The bellows 20, which may be fabricated by molding of a lightweight, flexible material such as polyethylene, preferably has a square cross-section to provide an interior chamber 26 of volume sufficiently large for inhalation exercises yet having moderate height and cross-sectional dimensions. A suitable wall thickness for the bellows is about tem mils at the inner parts of the convolutions decreasing to about five mils at the outer extremities of the convolutions, although portions of the upper and lower ends may be substantially thicker. The upper end terminates in a cylindrical neck 28 (see FIG. 3) shaped to fit tightly within a collar 30 of the upper housing member 22. The bellows 20 is held in place by contact between the collar 30 and the neck 28 and by means of a lock tab 32 projecting outward from the top of the neck 28.

To permit withdrawal of air from the interior chamber 26 defined by the bellows 20, a port 34 is provided in the top of the neck 28. The port 34 communicates through a hollow portion 36 of the top housing member 22 with a flexible inhalation tube 38 which is attachable to an outlet 40 of the member 22. As shown in FIG. 3, the inhalation tube 38 includes a mouthpiece 42 at one end, and also contains a porous filter 44 for assuring that no foreign material enters the lungs of a patient. Preferably the connection between the tube 38 and the outlet 40 of the housing member 22 is a simple attachment such as a locking taper so that the tube 38 may be easily removed and stored in an annular groove 46 in the housing member 22 when the exerciser is not in use.

The inhalation exerciser includes other structural members to facilitate measurement of the volume of air inspired by a patient and for convenience in handling the device. As shown in FIGS. 1-3, a bottom housing member 50 surrounds the extended lower end 24 of the bellows 20 and is held in place by two side arms 52 and 54 connected to both housing members 22 and 50. Both the housing members and side arms are preferably rigid parts made by molding a suitable plastic material. The arm 52 on the side of the exerciser to which the inhalation tube 38 is attachable includes a scale 56 for measuring the volume of air withdrawn from the bellows 20. The volume withdrawn, which is equal to the volume of air inspired by a patient, may be determined by reading the scale 56 at the point at which it is aligned with the lower end 24 of the bellows 20. A slide ring 58 may be mounted on the side arm 52 to provide a goal for the patient or to record the inspired volume achieved.

Figure 5:
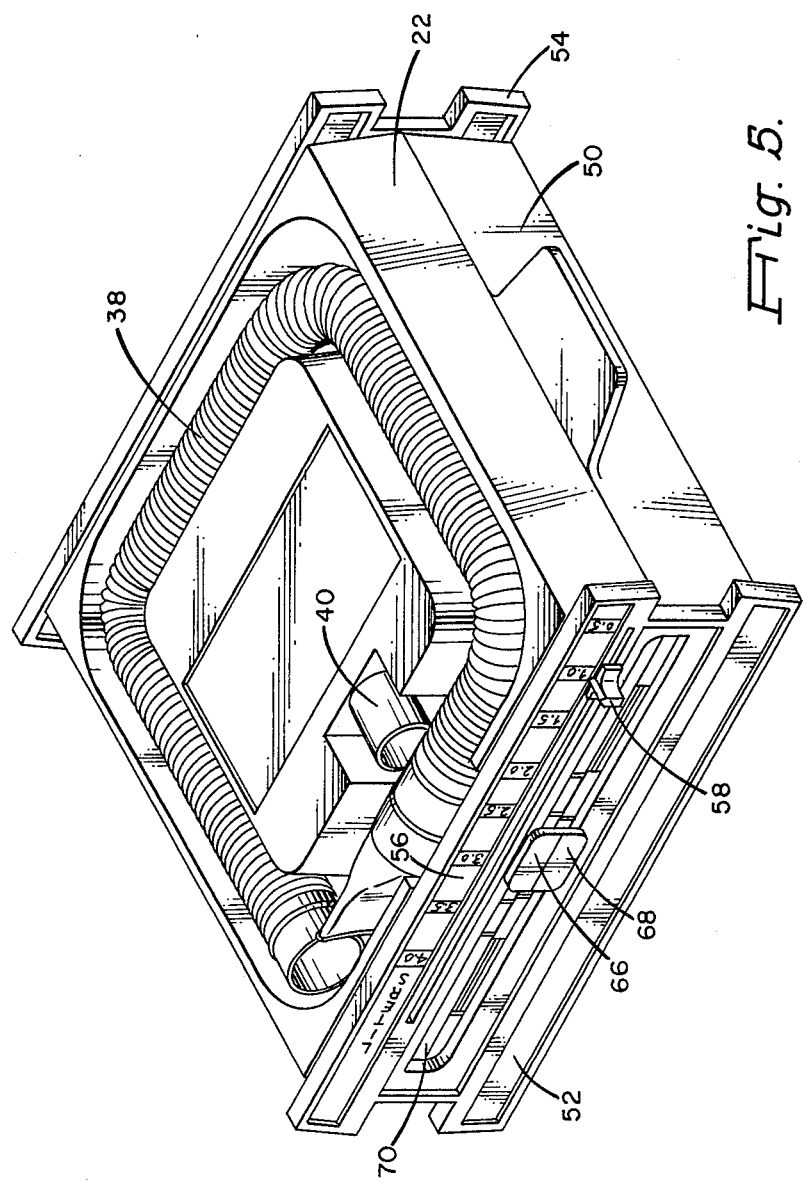
FIG. 5 is a perspective view of the inhalation device of FIG. 1 in a collapsed form suitable for storage.
Figure 6:
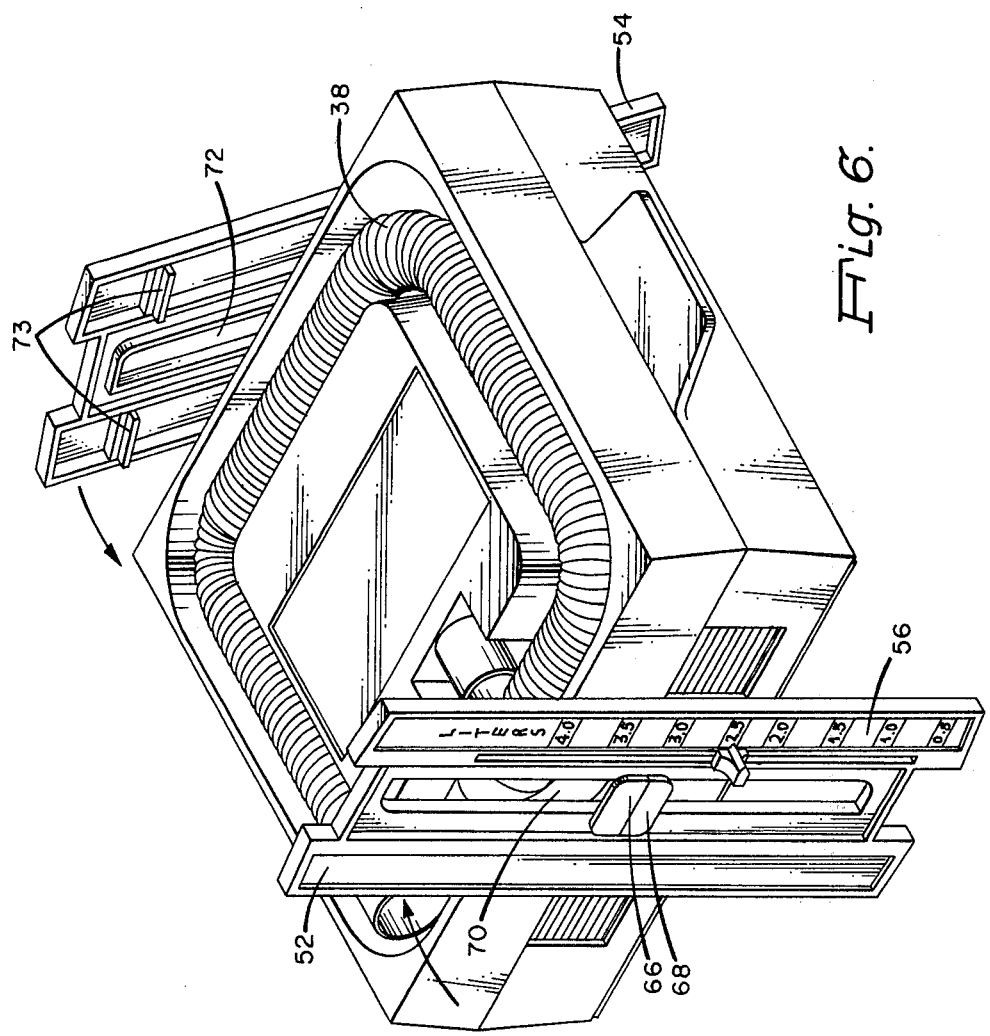
FIG. 6 is a perspective view of the inhalation device in a position intermediate between those shown in FIGS. 1 and 5 and illustrating a step in preparing the device for storage.

To minimize the storage and shipping volume required for the inhalation device, the connections between the side arms 52 and 54 and the housing members 22 and 50 are selected so as to accommodate rotational and sliding movement of the housing members relative to the side arms. This permits the inhalation device to be readily converted from a form suitable for exercises (i.e., the deployed form shown in FIGS. 1-3, 6) to a compact or collapsed form (FIG. 5) occupying a substantially reduced volume such as about one-third that of the deployed exerciser. In the preferred exerciser the top housing member 22 and the bottom housing member 50 both include an ear-like tab projecting from each of their two opposed sides adjacent to the arms 52 and 54. The tab 66 of top housing member 22 and the tab 68 of bottom housing member 50, as well as similar tabs (not shown) adjacent the arm 54, are shaped for slidable retention in elongated slots 70 and 72 provided in arms 52 and 54, respectively.

When the exerciser is in the deployed form, the arms 52 and 54 are parallel to the direction of movement of the bellows 20, and locking tabs 73, 74, 75 and 76 located near the ends of the arms 52 and 54 (see FIGS. 3, 4, and 6) lock the housing members 22 and 50 at opposite ends of the slots 70 and 72. To convert the device to its compact form, the inhalation tube 38 is first removed from the outlet 40 and stored in the groove 46 of the top housing member 22. The housing members 22 and 50 are then freed from their locked positions and slid along the slots 70 and 72 to a position adjacent each other (FIG. 6), collapsing the bellows 20 therebetween. The side arms 52 and 54 may then be rotated 90 degrees clockwise to a position normal to the direction of bellows movement during use, completing the conversion to compact form.

The flexibility of storing the exerciser in a compact form is of considerable benefit not only in shipping the inhalation exercisers but also in maintaining an adequate supply of the disposable devices in hospitals or other facilities where storage space is rather limited. Also, the easy convertibility of the exerciser from compact form to deployed form without having to connect several individual parts considerably simplifies the tasks of therapists and users of the device.

Retention of the bellows 20 in a retracted or collapsed position for a period of time such as during shipment or storage, particularly in areas subject to elevated temperatures, may result in stress relief of the bellows such that the bellows acquires a cold set. Polyethylene, a preferred bellows material because it is flexible, easily fabricable, and inexpensive, has been found susceptible to cold-setting, which could interfere with movement of the bellows during use. Accordingly, biasing means are provided to assure return of the lower end 24 of the bellows 20 to its fully extended position. Preferably, the biasing means comprises a steel disk 80 with a central hole therein which permits the disk to be snapped over and held by a raised portion 84 of the lower end 24 of the bellows. The steel disk 80 is of a weight sufficient to return the bellows 20 to its fully extended position when the mouthpiece 42 is removed from a patient's mouth, yet is light enough to allow the lower end 24 of the bellows to deflect upward in response to even a small pressure drop induced by inhalation. Other biasing means such as springs could be employed; however, springs are less suitable because of added complexity and because the inhalation force required to move the bellows would vary substantially with bellows position.

The breathing exerciser is used by first converting it from compact form to deployed form, if necessary, and placing it on a horizontal surface. The patient inhales through the mouthpiece 42, withdrawing air from the interior chamber 26 of the bellows 20. This causes the lower end 24 of the bellows 20 to move upward towards the top housing member 22, and the true volume of air inhaled may be accurately determined by the alignment of the lower end 24 with the markings on the scale 56. When the patient has finished inhaling—e.g. he attains the volume indicated as a goal by the preset position of the slide ring 58, he holds his breath for a desired time interval according to an established program of therapy. Since no leak holes or bleed orifices are provided in the exerciser, the bellows 20 will then remain in its deflected position for as long as the breath is held, confirming that the patient is holding his breath according to the prescribed exercise.

While the invention has been shown and described with reference to preferred embodiments thereof, it is apparent that the inhalation device may be embodied in other specific forms without departing from the spirit or essential characteristics of the invention. The scope of the invention is indicated by the appended claims, and all changes which come within the meaning and range of equivalency of these claims are intended to be embraced therein.

What is claimed is:

1. An inhalation device comprising:
a top housing member;
a bellows including an upper end attached to said top housing member and a lower end, said lower end being movable during use between an extended bellows position remote from said top housing member and a retracted bellows position adjacent to said top housing member, said lower end also being retainable in said retracted bellows position for facilitating storage of the device in compact form;
means for permitting withdrawal of air from the interior of said bellows;
means for measuring the volume of air withdrawn from said bellows;
a bottom housing member mounted in opposed relationship to said top housing member such that the bellows is positioned therebetween, said bottom housing member and said top housing member each including a tab projecting from each of two opposed sides thereof; and
a pair of side arms supportably connecting said bottom housing member and said top housing member, each of said arms having an elongated slot therein receiving and slidably retaining one of the tabs of each of said housing members.

2. An inhalation device as in claim 1 wherein said bellows is airtight except for a port defined in the upper end thereof and in communication with said means for permitting withdrawal of air from the interior of said bellows.

3. An inhalation device as in claim 2 wherein said means for permitting withdrawal of air includes an inhalation tube attached to said top housing member and defining with said top housing member an air passageway in communication with the port of said bellows.

4. An inhalation device as in claim 1 further including biasing means attached to the lower end of said bellows for urging said lower end of the bellows away from said top housing member towards said extended bellows position.

5. An inhalation device as in claim 1 wherein said means for measuring the volume of air withdrawn from said bellows comprises a scale on at least one of said side arms, said scale being alignable with the lower end of said bellows.

6. An inhalation device as in claim 1 wherein said arms include means for locking said top and bottom housing members at opposite ends of said slots.

7. An inhalation device as in claim 6 wherein said bellows and said housing members each has a substantially square cross-section, said arms are positioned adjacent opposed sides of said bellows, and each of said arms includes an inner surface facing said bellows and an outer surface facing away from said bellows.

8. An inhalation device as in claim 7 wherein the outer surface of each of said arms includes a recessed portion surrounding said slot and adapted to guide said tabs during sliding movement thereof, said recessed portion having a width slightly greater than the longest dimension of said tabs to permit rotation of said tabs within said recessed portion, thereby to facilitate conversion of said device without disassembly from a deployed configuration wherein said arms are in a position parallel to the direction of movement of the lower end of said bellows during use and said top and bottom housing members are locked at opposite ends of said slots, to a storage configuration wherein said side arms are in a position normal to said direction of bellows movement and said top and bottom housing members are adjacent to each other.

* * * * *